US006462191B1

(12) United States Patent
Lal

(10) Patent No.: US 6,462,191 B1
(45) Date of Patent: Oct. 8, 2002

(54) SYNTHESIS OF 2-DEOXY-2-FLUORO-ARABINOSE DERIVATIVES

(75) Inventor: Gauri Sankar Lal, Whitehall, PA (US)

(73) Assignee: Air Products and Chemicals, Inc., Allentown, PA (US)

(*) Notice: Subject to any disclaimer, the term of this patent is extended or adjusted under 35 U.S.C. 154(b) by 12 days.

(21) Appl. No.: 09/615,877

(22) Filed: Jul. 13, 2000

(51) Int. Cl.[7] .......................... C07H 1/00; C07G 11/00; C07G 3/00

(52) U.S. Cl. ...................... 536/122; 536/1.11; 536/4.1; 536/125

(58) Field of Search ................ 536/1.11, 4.1, 536/122, 125

(56) References Cited

U.S. PATENT DOCUMENTS

| 6,080,886 A | 6/2000 | Lal et al. .................... 560/227 |
| 6,207,860 B1 | 3/2001 | Lal et al. .................... 564/102 |

OTHER PUBLICATIONS

Wright, et al., 13(2) J. Med. Chem. 269–72 (1970).
Fanucchi, et al., 69(1) Cancer Treat. Res. 55–9 (1985).
Fox, et al., Medicinal Chemistry Advances, p. 27 (Pergamon Press, NY, 1981).
Fox, et al., "Herpes Viruses and Virus Chemotherapy," Pharmacological and Clinical Approaches, p. 53, (Excerpta Medica, Amsterdam, 1985).
Lopez, et al., 17(5) J. Antimicrob. Agents Chemother. 803–6 (1980).
Lin, et al., 221 Science 619 (1983).
Chu, et al., 37 Chem. Pharm. Bull. 336 (1989).
Marquez, et al., 33 J. Med. Chem. 978 (1990).
Boswell, et al., 21 Org. React. 1 (1974).
Lal, et al., 64(19) J. Org. Chem. 7048 (1999).
Lal, et al., J. Chem. Soc. Chem. Commun., p. 215 (1999).
Fox, 18 J. Pure Appl. Chem., 223 (1969).
Pankiewicz, et al., 64 J. Fl. Chem. 15 (1993).
Pankiewicz, et al., 57 J. Org. Chem. 553 (1992).
Pankiewicz, et al., 15 J. Fl. Chem. 64 (1993).
Reichmann, et al., 42 J. Cardohydr. Res. 233 (1975).
Tann, et al., 50 J. Org. Chem. 3644 (1985).
Welch, et al., *Fluorine in Bioorganic Chemistry*, p. 131 (John Wiley and Sons, 1991).
Chou, et al., (37 Tett. Lett. 1 (1996)).
Hudlicky, M., Org. React., p. 519, 522–524, 543–545 (1988).
Sutherland, et al., *The First Isolation of an Alkoxy–N, N–dialkylaminodifluorosulfane from the Reaction of an Alcohol and DAST: an Efficient Synthesis of (2S,3R, 6S)–3–Fluoro–2,6–Diaminopimelic Acid*, p. 1739–1740, (Chem. Commun., 1999).

*Primary Examiner*—Jezia Riley
(74) *Attorney, Agent, or Firm*—Geoffrey L. Chase

(57) ABSTRACT

A process for deoxofluorinating a $C_2$-hydroxyl group of a furanose, includes: (a) mixing the furanose and a deoxofluorinating agent in a solvent to form a reaction mixture, and (b) heating the reaction mixture to greater than about 50° C. The process provides deoxofluorinated products, such as 2-fluoro-arabinoses, in yields of at least 80% of theoretical.

24 Claims, No Drawings

US 6,462,191 B1

SYNTHESIS OF 2-DEOXY-2-FLUORO-ARABINOSE DERIVATIVES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to processes for deoxyfluorinating the pentose sugar of a nucleoside to form the corresponding 2-β-fluoro-arabinose compounds.

The development of safe, efficient, and simple methods for selective incorporation of fluorine into organic compounds has become a very important area of technology. It is of particular importance with respect to the deoxyfluorination of the pentose sugar component of a nucleoside to form 2-β-fluoro-arabinose compounds, which have been shown to exhibit potent anti-tumor and anti-viral activity. See, e.g., Wright et al., 13(2) J. Med. Chem. 269–72 (1970); Fanucchi et al., 69(1) Cancer Treat. Res. 55–9 (1985); Fox et al., Medicinal Chemistry Advances, p. 27 (Pergamon Press, NY, 1981); and Fox et al., "Herpes Viruses and Virus Chemotherapy," Pharmacological and Clinical Approaches, p. 53, (Excerpta Medica, Amsterdam, 1985). For example, 2'-fluoro-5-iodo-ara-cytosine (FIAC), 2'-fluoro-5-methyl-ara-uracil (FMAU), 2'-fluoro-5-methyl-ara uracil (FMAU) and 2'-fluoro-5-ethyl-ara uracil (FEAU) are active against DNA viruses, according to Lopez et al., 17(5) J. Antimicrob. Agents Chemother. 803–6 (1980); and Lin et al., 221 Science 519 (1983). Although certain 2'-fluoropurine derivatives are cytotoxic, others have been shown to possess anti-HIV activity. See, e.g., Chu et al., 37 Chem. Pharm. Bull. 336 (1989); and Marquez et al., 33 J. Med. Chem. 978 (1990). This is due to the fact that fluorine strategically positioned at sites of synthetic drugs and agrochemical products can significantly modify and/or enhance their biological activities. Fluorine mimics hydrogen with respect to steric requirements and contributes to an alteration of the electronic properties of the molecule. Increased lipophilicity and oxidative and thermal stabilities have been observed in such fluorine-containing compounds.

The conversion of the C—O bond to the C—F bond, which is referred to herein as deoxofluorination, represents a viable method to produce selectively fluorinated organic compounds. Deoxofluorination represents one technique which has been widely used for the selective introduction of fluorine into organic compounds. See, e.g., Boswell et al., 21 Org. React. 1 (1974). A list of the deoxofluorination methods generally used to fluorinate organic compounds to date includes: nucleophilic substitution via the fluoride anion; phenylsulfur trifluoride; fluoroalkylamines; sulfur tetrafluoride; $SeF_4$; $WF_6$; difluorophosphoranes and the dialkylaminosulfur trifluorides (DAST). The most common reagent of this class is diethylaminosulfur trifluoride, Et-DAST or simply DAST.

The DAST compounds have proven to be useful reagents for effecting deoxofluorinations. These reagents are conventionally prepared by reaction of N-silyl derivatives of secondary amines with $SF_4$. In contrast to $SF_4$, DAST compounds are liquids which can be used at atmospheric pressure and at near ambient to relatively low temperature (room temperature or below) for most applications. Deoxofluorination of alcohols and ketones is particularly facile and reactions can be carried out in a variety of organic solvents (e.g., $CHCl_3$, $CFCl_3$, glyme, diglyme, $CH_2Cl_2$, hydrocarbons, etc.). Most fluorinations of alcohols are done at a temperature within the range of −78° C. to room temperature. Various functional groups are tolerated, including CN, $CONR_2$, COOR (where R is an alkyl group), and successful fluorinations have been accomplished with primary, secondary and tertiary (1°, 2°, 3°) allylic and benzylic alcohols. The carbonyl to gem-difluoride transformation is usually carried out at room temperature or higher. Numerous structurally diverse aldehydes and ketones have been successfully fluorinated with DAST. These include acyclic, cyclic, and aromatic compounds. Elimination does occur to a certain extent when aldehydes and ketones are fluorinated and olefinic byproducts are also observed in these instances.

However, while the DAST compounds have shown versatility in effecting deoxofluorinations, there are several well-recognized limitations associated with their use. The compounds can decompose violently and while adequate for laboratory synthesis, they are not practical for large scale industrial use. In some instances, undesirable byproducts are formed during the fluorination process. Olefin elimination byproducts have been observed in the fluorination of some alcohols. Often, acid-catalyzed decomposition products are obtained. Moreover, the two-step synthesis employed with DAST compounds renders these relatively costly compositions only suitable for small scale syntheses.

The inventor and his colleagues have previously disclosed that other aminosulfur trifluorides, such as bis(2-methoxyethyl)aminosulfur trifluoride, are much safer to use than DAST and related aminosulfur trifluorides. See Lal et al., 64(19) J. Org. Chem. 7048 (1999); Lal et al., J. Chem. Soc. Chem. Commun. p. 215 (1999); U.S. Pat. No. 6,080,886 and U.S. patent application Ser. No. 08/939,635 filed Sep. 29, 1997. Compared to DAST compounds, bis(2-methoxyethyl)aminosulfur trifluorides provide more thermally stable fluorine-bearing compounds which have effective fluorinating capability with far less potential of violent decomposition and attendant high gaseous byproduct evolvement, with simpler and more efficient fluorinations. Furthermore, bis(2-methoxyethyl)aminosulfur trifluorides can efficiently effect the transformation of hydroxy and carbonyl functionalities to the corresponding fluoride and gem-difluoride respectively.

It has been observed that the direct replacement of a leaving group at the 2'-position of a pyrimidine nucleoside by the fluoride ion is complicated by neighboring-group participation of the carbonyl group of the base, resulting in the formation of the anhydronucleoside. See Fox, 18 J. Pure Appl. Chem. 223 (1969). In the synthesis of 2'-fluoropurines, attempts to replace a $C_2$ protecting group (e.g., triflate) with fluoride resulted in base cleavage and formation of olefinic byproducts. See Pankiewicz et al., 64 J. Fl. Chem. 15 (1993). It has also been observed that the direct deoxofluorination of the 2'-hydroxyl of some purine derivatives by diethylaminosulfur trifluoride (DAST) afford only low yields of products even when a large excess of the fluorinating agent is used. See Pankiewicz et al., 57 J. Org. Chem. 553 (1992).

The synthesis of 2'-fluoro-substituted nucleosides is currently carried out by condensation of the appropriate 2-fluoro sugar derivative with the nucleoside base. See Pankiewicz et al., 15 J. Fl. Chem. 64 (1993). However, the fluoro sugar is not easily accessible since its preparation often involves lengthy multi-step and low yielding procedures. See Reichmann et al., 42 J. Cardohydr. Res. 233 (1975). The nucleophilic displacement of a leaving group by fluoride at C-2 of furanosides is often accompanied by elimination reactions resulting in olefinic byproducts. See Tann et al., 50 J. Org. Chem. 3644 (1985). Tann et al. reported on a three-step synthesis of 2-deoxy-2-fluoro-1,3, 5-tri-O-benzoyl-α-D-arabinofuranose via a 2-O-imidazolylsulfonate leaving group using $KHF_2$ as the source of fluoride. Tann et al. found that the direct replacement of the $C_2$-hydroxyl of this sugar by F with diethylaminosulfur trifluoride (DAST) failed.

Despite the findings in Tann et al., it has been shown that DAST has been used successfully for the deoxofluorination of hydroxy groups of six-membered ring sugars and the $C_3$ hydroxyl of five-membered ring sugars (i.e., furanoses). See Welch et al., *Fluorine in Bioorganic Chemistry*, p. 131 (John Wiley and Sons, 1991). Additionally, the procedure of Tann et al. was improved upon by Chou et al. (37 Tett. Lett. 1 (1996)) where triethylamine poly(hydrogen fluoride) was used as the source of fluoride.

Accordingly, there remains a need in the art for a process effective to deoxofluorinate the $C_2$-hydroxyl group of furanoses.

All references cited herein are incorporated herein by reference in their entireties.

BRIEF SUMMARY OF THE INVENTION

The invention provides a process for deoxofluorinating a $C_2$-hydroxyl group of a furanose. The process comprises mixing the furanose and a deoxofluorinating agent in a solvent to form a reaction mixture, and heating the reaction mixture to greater than about 50° C.

Also provided are products produced by the process of the invention.

BRIEF DESCRIPTION OF SEVERAL VIEWS OF THE DRAWINGS

Not applicable.

DETAILED DESCRIPTION OF THE INVENTION

A preferred process of the invention comprises deoxyfluorinating a hydroxylated ring carbon of a sugar with a fluorinating agent in the presence of a solvent. A preferred embodiment of the invention is shown in Equation I:

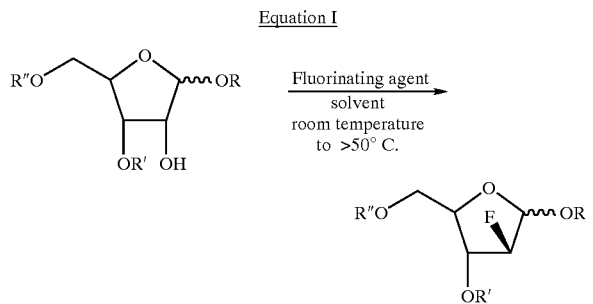

Equation I where each of R, R' and R" is independently a protecting group or a group that does not react with the deoxofluorinating agent in the inventive process (unless it is desired to deoxofluorinate more than one carbon per molecule). Preferred protecting groups include esters, ethers, sulfonates, acetals and orthoesters. Particularly preferred protecting groups include benzoyl, trityl and triflate.

In embodiments, it is preferred to further modify the product of deoxofluorination to replace the protecting groups with hydrogen and/or to convert the sugar into a 2'-deoxy-2'-fluoro-arabinoside, wherein R of Equation I is a pyrimidine (e.g., cytosine, uracil or thymine) or a purine (e.g., adenine or guanine). Methods for coupling the sugar with a nucleoside base are known in the art. Thus, the invention provides an improved process for providing 2'-fluoropurines and 2'-fluoropyrimidines. The most preferred embodiments of the inventive process provide 2-fluoro-arabinose compounds and derivatives, including those previously shown to exhibit potent anti-tumor and anti-viral activity.

The preferred reactant to be deoxofluorinated is a five-membered ring sugar (i.e., a furanose) bearing a hydroxyl group solely at $C_2$, wherein any additional hydroxyl groups have been replaced with a protecting group. Ribofuranoses are preferred reactants, but the invention is not limited thereto. For example, furanoses wherein $C_3$ is unsubstituted (i.e., is bonded to two hydrogens) are also suitable reactants. The choice of reactant is largely influenced by the desired product. Ribofuranose reactants are most preferred as they provide 2-fluoro-arabinose products, such as 2-fluoro-1,3,5-tribenzoyl-α-D-arabinofuranose, 3-deoxy-2-fluoro-1-methoxy-5-trityl-α-D-arabinofuranose, and 2-fluoro-1,3,5-tribenzoyl-α-L-arabinofuranose, which are preferred products of the invention.

After having the hydroxyl groups other than the $C_2$ hydroxyl group protected (or selecting a sugar inherently containing groups other than the $C_2$ hydroxyl group which are not reactive with the deoxofluorinating agent), the sugar to be deoxofluorinated is reacted with a deoxofluorinating agent in a solvent. Deoxofluorinating agents suitable for use in the invention include, e.g., diethylaminosulfur trifluoride (DAST), bis(2-methoxyethyl)aminosulfur trifluoride (Deoxo-Fluor™ reagent available from Air Products and Chemicals, Inc., Allentown, Pa.), perfluorobutanesulfonyl fluoride, 2-chloro-1,2,3-trifluoroethyldiethylamine (Yarovenko-Raksha reagent), and hexafluoroisopropyl diethylamine (Ishikawa reagent) and other aminosulfur trifluorides. Preferably, the deoxofluorinating agent is bis(2-methoxyethyl)aminosulfur trifluoride.

The deoxofluorination reaction of the present invention is conducted in the presence of a solvent. Preferably, the solvent does not react with the fluorinating agent. More preferably, the solvent is selected from the group consisting of hydrocarbons, halocarbons, ethers, amides, esters and mixtures thereof. Most preferably, the solvent is toluene. The solvent is preferably non-polar.

Preferably, the deoxofluorination is conducted at temperatures ranging from room temperature to less than the boiling point of the solvent. It is particularly preferred to combine the reactants in the solvent at room temperature and allow the reaction to progress at room temperature (i.e., without active heating) for a period of time before raising the temperature above 50° C.. The mixing time without active heating is about 30 to 90 minutes, preferably about 1 hour. After this initial reaction period, the reaction mixture is preferably heated to greater than about 50° C., more preferably about 90° C., and mixed for an additional 90 minutes or more, preferably about 2 hours.

Thus, in particularly preferred embodiments, the reactants are combined in the solvent at room temperature, mixed without heating for about 1 hour, and heated to about 90° C. with continued mixing for an additional 2 hours or so.

The reaction product is preferably isolated from the reaction mixture by quenching the reaction with an aqueous base, extracting the product in an organic solvent and distilling the solvent. The aqueous base is preferably NaHCO$_3$. The solvent used for extraction is preferably the same solvent used as a medium for the reaction.

The product can be further purified by conventional techniques, such as chromatography or recrystallization.

Unlike conventional methods, the instant invention provides 2-fluoro-arabinose compounds in a yield ranging from about 83% to about 98% of theoretical.

The invention will be illustrated in more detail with reference to the following Examples, but it should be understood that the present invention is not deemed to be limited thereto.

EXAMPLES

Example 1

Fluorination of 1,3,5-tribenzoyl-α-D-ribofuranose with Bis(2-methoxyethyl)aminosulfur Trifluoride A suspension of 1,3,5-tribenzoyl-α-D-ribofuranose (225 mg, 0.5 mmol) in toluene (5 mL) was treated with bis(2-methoxyethyl)aminosulfur trifluoride (110 mg, 0.5 mL) under nitrogen in a 50 mL 3-neck round bottom flask equipped with a N$_2$ inlet, a rubber septum, a stopper and a magnetic stir bar. The mixture was stirred at room temperature for 1 hour. It was then heated to 90° C. and kept at this temperature for an additional 2 hours. The solution was cooled to 0° C. and treated with saturated NaHCO$_3$ solution. After CO$_2$ evolution ceased, the mixture was extracted with toluene, dried (Na$_2$SO$_4$), filtered and evaporated in-vacuo. The residue was purified by chromatography on silica gel in ethyl acetate/hexanes (1/4) to obtain 215 mg (95% yield) of pure 2-deoxy-2-fluoro-1,3,5-tri-O-benzoyl-α-D-arabinofuranose (Formula I, below, where Bz represents C—O-Phenyl).

Formula I

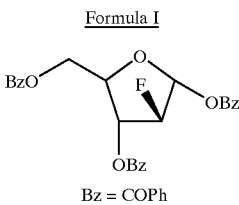

Bz = COPh

The NMR spectral characteristics obtained were $^1$H NMR (CDCl$_3$) d 8.2–7.95 (m, 6H), 7.75–7.5 (m, 3H), 7.5–7.35 (m, 6 H), 6.75 (d, 1H, J=9 Hz), 5.65 (dd, 1H, J=18 Hz, 3 Hz), 5.35 (d, 1H, J=48 Hz), 4.85–4.75 (m, 1H), 4.75–4.65 (m, 2H). $^{19}$F NMR (CDCl$_3$) d–191.

Example 2

Fluorination of 1,3,5-tribenzoyl-α-D-ribofuranose with DAST

Deoxofluorination was performed as in Example 1, with DAST (80 mg, 0.5 mL) substituted for bis(2-methoxyethyl) aminosulfur trifluoride. The reaction yielded 217 mg (96% yield) of 2-deoxy-2-fluoro-1,3,5-tri-O-benzoyl-α-D-arabinofuranose (Formula I, above). The NMR spectral characteristics were the same as in Example 1.

Example 3

Fluorination of 3-deoxy-1-methoxy-5-trityl-α-D-ribofuranoside with Bis(2-methoxyethyl) aminosulfur Trifluoride Deoxofluorination of 3-deoxy-1-methoxy-5-trityl-α-D-ribofuranoside (388 mg, 1 mmol) was performed as in Example 1, using 243 mg (1.1 mmol) of bis(2-methoxyethyl)aminosulfur trifluoride in 5 mL of toluene. The reaction yielded 324 mg (83% yield) of 3-deoxy-2-fluoro-1-methoxy-5-trityl-α-D-arabinofuranose (Formula II, below) as a mixture of anomers.

Formula II

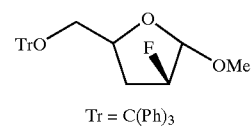

Tr = C(Ph)$_3$

The NMR ($^1$H NMR (CDCl$_3$)) spectral characteristics obtained were: (major anomer) d 7.5–7.3 (m, 4.5 H), 7.3–7.1 (m, 4.5 H), 7.1–7.0 (m, 2.25 H), 5.0 (d, 0.75 H), 4.8 (dm, 0.75 H), 4.35–4.10 (m, 0.75), 3.3–3.0 (m, 1.5 H), 3.3 (s, 2.25H), 2.4–2.1 (m, 0.75H), 1.9–1.7 (m, 0.75 H). $^{19}$F NMR d–180. $^1$H NMR (CDCl$_3$) (minor anomer), d d 7.5–7.3 (m, 1.5 H), 7.3–7.1 (m, 1.5 H), 7.1–7.0 (m, 0.75 H), 5.0 (d, 0.25 H), 4.9 (dm,0.25 H), 4.35–4.10 (m, 0.25 H), 3.7–3.5 (m, 0.5H), 3.3 (s, 0.75H) 1.8–1.3 (m, 0.5H). $^{19}$F NMR (CDCl3) –180.

Example 4

Fluorination of 1,3,5-tribenzoyl-α-L-ribofuranoside with Bis(2-methoxyethyl)aminosulfur Trifluoride Deoxofluorination of 1,3,5-tribenzoyl-α-L-ribofuranoside (4.5 g, 10 mmol) was performed as in Example 1, using 2.43 g (11 mmol) of bis(2-methoxyethyl) aminosulfur trifluoride in 50 mL of toluene. The reaction yielded 4.87 g (98% yield) of 2-fluoro-1,3,5-tri-O-benzoyl-α-L-arabinofuranose, having spectral characteristics similar to the (D)-isomer product of Example 1.

Comparative Example

The procedure employed in the foregoing examples to prepare 2-fluoroarabinose derivatives was found to be rather facile, despite the teachings of Tann et al., supra, to the effect that the direct replacement of the C$_2$-hydroxyl of 2-deoxy-2-fluoro- 1,3,5-tri-O-benzoyl-α-D-arabinofuranose by F with diethylaminosulfur trifluoride (DAST) failed. An experiment was performed to confirm the result reported by Tann et al.

A suspension of 1,3,5-tri-O-benzoyl-α-D-ribofuranose (225 mg, 0.5 mmol) in CH$_2$Cl$_2$ (5 mL) was treated with DAST (81 mg, 0.067 mL). The mixture was stirred at room temperature to reflux. After 16 hours, a hard to resolve, complex mixture of fluorinated products was observed with an approximately 40% yield of the desired 2-fluoro-arabinose.

It is apparent from the foregoing examples and comparative example that the inventive process is a simple, yet powerful, tool for obtaining deoxofluorinated sugars, such as 2-deoxy-2-fluoro-arabinoses, and derivatives thereof, including nucleosides. The inventive process even works quite well with a 3-deoxyribose bearing an acid sensitive trityl group at C$_5$ and a methoxy group at the anomeric carbon (Example 3). Even with this compound, no elimination products were observed.

It has been noted that the process favors a relatively non-polar reaction medium, since in more polar solvents such as CH$_3$CN and DMF, none of the desired products were observed.

There has been some speculation in the literature on the mechanism of deoxofluorination of alcohols by aminosulfur trifluorides. While there has been some NMR evidence for the formation of an alkoxy-N,N-dialkylaminodifluorosulfurane intermediate, it was only recently that such a specie was isolated and fully characterized. See Sutherland et al., Chem. Commun. 1739 (1999). The stability of the difluorosulfurane intermediate seems to be greater for alcohols that are more sterically hindered. The results obtained in the fluorination of the 2-hydroxyribose derivatives in the present invention suggest that a relatively stable alkoxy-N,N-dialkylaminodifluorosulfurane interemediate is formed at lower temperatures as a result of the steric influence of the vicinal α-protecting groups. This is subsequently displaced by fluoride on heating to higher temperatures leading to the desired 2'-fluoro product.

While the invention has been described in detail and with reference to specific examples thereof, it will be apparent to one skilled in the art that various changes and modifications can be made therein without departing from the spirit and scope thereof.

What is claimed is:

1. A process for deoxofluorinating a $C_2$-hydroxyl group of a furanose, said process comprising:
   mixing said furanose and a deoxofluorinating agent in a solvent to form a reaction mixture; and
   heating said reaction mixture; quenching said deoxofluorinating agent in said heated reaction mixture to provide a quenched mixture; and
   isolating a deoxofluorinated product from said quenched mixture, wherein a yield of said deoxofluorinated product is at least 80% of theoretical.

2. The process of claim 1, wherein said yield is at least 95%.

3. The process of claim 1, wherein said mixing is conducted for 30 to 90 minutes without active heating.

4. The process of claim 1, wherein said mixing is conducted for about 1 hour without active heating.

5. The process of claim 1, wherein said heating is conducted for at least 90 minutes.

6. The process of claim 1, wherein said heating is conducted for about 2 hours.

7. The process of claim 1, wherein said reaction mixture is heated to about 90° C.

8. The process of claim 1, wherein said mixing is conducted for about 1 hour, and then said heating is conducted for about 2 hours at about 90° C.

9. The process of claim 1, wherein said solvent is non-polar.

10. The process of claim 1, wherein said solvent is at least one member selected from the group consisting of halocarbons, hydrocarbons, ethers, amides and esters.

11. The process of claim 1, wherein said solvent is toluene.

12. The process of claim 1, further comprising the step of substituting a protecting group for each hydroxyl group of said furanose other than said $C_2$-hydroxyl group.

13. The process of claim 12, wherein said protecting group is at least one member selected from the group consisting of esters, ethers, sulfonates, acetals and orthoesters.

14. The process of claim 12, wherein said protecting group is at least one member selected from the group consisting of benzoyl, trityl or triflate.

15. The process of claim 12, wherein said furanose an arabinofuranose.

16. The process of claim 12, wherein said furanose is a ribofuranose.

17. The process of claim 16, wherein said furanose is 1,3,5-tribenzoyl-α-D-ribofuranose, 1,3,5-tribenzoyl-α-L-ribofuranose or 3-deoxy-1-methoxy-5-trityl-α-D-ribofuranose.

18. The process of claim 16, wherein a product of said deoxofluorinating is a 2-deoxy-2-fluoro-arabinofuranose.

19. The process of claim 18, further comprising replacing a $C_1$ hydroxyl group with a pyrimidine or a purine.

20. A 2'-deoxy-2'-fluoro-arabinofuranoside produced by the process of claim 19.

21. A 2-deoxy-2-fluoro-arabinofuranose produced by the process of claim 18.

22. A process for deoxofluorinating a $C_2$-hydroxyl group of a furanose, said process comprising:
   mixing said furanose and a deoxofluorinating agent in a solvent to form a reaction mixture; and
   heating said reaction mixture,
   wherein said deoxofluorinating agent is an aminosulfur trifluoride.

23. The process of claim 22, wherein said deoxofluorinating agent is at least one member selected from the group consisting of diethylaminosulfur trifluoride, bis(2-methoxyethyl) aminosulfur trifluoride, perfluorobutanesulfonyl fluoride, 2-chloro-1,2,3-trifluoroethyldiethylamine and hexafluoroisopropyl diethylamine.

24. The process of claim 23, wherein said deoxofluorinating agent is bis(2-methoxyethyl) aminosulfur trifluoride.

* * * * *